United States Patent
Vandenberg

(10) Patent No.: US 8,324,259 B2
(45) Date of Patent: Dec. 4, 2012

(54) FUNGICAL CONTROL OF MOULDS

(75) Inventor: Edwin Vandenberg, Ontario (CA)

(73) Assignee: Bayer Cropscience Inc., Calgary, Alberta (CA)

( * ) Notice: Subject to any disclaimer, the term of this patent is extended or adjusted under 35 U.S.C. 154(b) by 0 days.

(21) Appl. No.: 13/024,524

(22) Filed: Feb. 10, 2011

(65) Prior Publication Data

US 2011/0144173 A1 Jun. 16, 2011

Related U.S. Application Data

(62) Division of application No. 12/090,238, filed as application No. PCT/CA2005/001608 on Oct. 19, 2005.

(51) Int. Cl.
*A01N 43/50* (2006.01)
*A01P 3/00* (2006.01)

(52) U.S. Cl. .................................. 514/389; 424/405

(58) Field of Classification Search .................. 514/389; 424/405
See application file for complete search history.

(56) References Cited

U.S. PATENT DOCUMENTS

| 3,755,350 | A | 8/1973 | Sauli |
| 3,823,240 | A | 7/1974 | Sauli |
| 5,238,956 | A | 8/1993 | Clough et al. |
| 6,057,331 | A | 5/2000 | Duvert |
| 6,639,097 | B1 | 10/2003 | De'Ath et al. |

FOREIGN PATENT DOCUMENTS

WO 98/54964 12/1998

OTHER PUBLICATIONS

EPA (Pesticide Fact Sheet, Trifloxystrobin, United States Environmental Protection Agency, 1999, p. 1-12).
Extoxnet (Extension Toxicology Network, Iprodione, 1993, p. 1-5).
International Search Report No. PCT/CA2005/001608, Mar. 15, 2006, 2 Pages.
Supplementary European Search Report Based on European Patent Application No. 05799484 Dated Nov. 28, 2008.
Extended European Search Report Based on Application No. 05799484.0-2103/1940230 Dated Dec. 19, 2008.
"Compass Specimen Label" [Online] May 18, 2001, p. 1-3, XP002505762; Retrieved From the Internet: URL:HTTP:// PESTICIDEINFO.ORG/REFERENCES/14 1517-21-7MSDS9_ 04.PDF> [Retrieved on Nov. 26, 2008].
United States Environmental Protection Agency: "Reregistration Eligibility Decision (RED) Iprodione" [Online] Nov. 1998, pp. 1-289, XP002505763.
European Office Action Based on Application No. 05799484.0-2103 Dated May 10, 2010.
Mocioni et al.; "Efficacy of Different Fungicides Against Rhizoctonia Brown Patch and Pythium Blight on Turfgrass in Italy"; XP009062268, Communications in Agricultural and Applied Biological Sciences, 68(4B), (Jan. 2003), 511-517.
Written Opinion of the International Searching Authority Based on PCT/CA2005/001608 Dated Mar. 16, 2006.
YES Interface Brochure FSRs; Interface Turf Management; Bayer Environmental Science; 2010; 8 pages; Bayer Cropscience LP.

*Primary Examiner* — San-Ming Hui
*Assistant Examiner* — Kathrien Cruz
(74) *Attorney, Agent, or Firm* — Baker Donelson Bearman, Caldwell & Berkowitz, PC

(57) ABSTRACT

A composition for treating fungus infection of turfgrass, such as snow mould infection, comprises a mixture of fungicidally effective amounts of formulae 1 and 2:

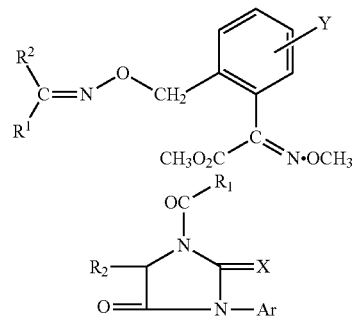

and in particular mixtures of iprodione and trifloxystrobin. A method for treating snow moulds comprises applying the mixture before the onset of continuous snow cover, in at least one application.

20 Claims, 4 Drawing Sheets

FUNGICAL CONTROL OF MOULDS

CROSS RELATED APPLICATIONS

This application is a Divisional of application Ser. No. 12/090,238, filed Jul. 16, 2010, which is a National Stage Application of PCT/CA05/001608 filed Oct. 19, 2005, the entire contents of which is hereby incorporated by reference in their entirety.

FIELD OF THE INVENTION

The present invention relates to the use of combinations of fungicides to control mould and related fungus infestations in grasses. In particular the present invention relates to the used of combinations of dicarboximide and 3-phenyl hydantoin fungicides and their formulations.

BACKGROUND OF THE INVENTION

Fine turfgrass species are grown on golf course greens, fairways and tee boxes, as well as turf farms and many other locations. In northern regions, such as Canada and the northern United States, which are subject to temperate climates in the late summer and early fall and snow conditions in late fall and early winter certain moulds such as dollar spot, *Sclerotinia homeocarpa*, and snow moulds, such as *Microdochium nivale, Typhula incarnate* and *Typhula ishikariensis*, represent a chronic problem for turfgrass growers. If left untreated in the late summer and fall, turfgrass is predisposed to damage caused by *Sclerotinia homeocarpa* in the late summer and fall and the snow moulds in late fall and over winter to spring. Where the mould infection is extensive, the recovery of the turfgrass can be delayed well into the growing season and seriously affect the ability of the turfgrass to recover, leaving areas of dead patches. Further, turfgrasses weakened or damaged by these moulds are extremely slow to recover in the spring and are often invaded by undesirable opportunistic weedy grass species such as creeping bentgrass (*Agrostis palustris*) and annual bluegrass (*Poa annua*).

A typical snow mould prevention program requires a mould inhibiting fungicide to be applied to turfgrass prior to permanent winter snow cover. Typical programs consist of three applications prior to permanent snow cover and an additional application after the snow cover is gone in the spring. Several commercial fungicide products have been approved for use against dollar spot and snow mould species, as will be described below.

Another fungus infection that afflicts turfgrass is dollar spot, a disease of turfgrasses caused by the fungus *Sclerotinia homeocarpa*. This species attacks most turfgrasses grown in the South. Bentgrass, hybrid bermudagrasses and zoysia are most susceptible to dollar spot. The disease occurs from spring through fall, and is most active during moist periods of warm days (70-85° F.) and cool nights (60° F.) in the spring, early summer and fall.

Rovral Green GT™ (iprodione; 3-(3,5-dichlorophenyl)-N-(1-methylethyl)-2,4-dioxo-1-imidazolidinecaboximide) is a dicarboximide fungicide registered in Canada for pink snow mould control at a rate of 250 ml/100 $m^2$ and for grey snow mould control at a rate of 375 ml/100 $m^2$. Iprodione is a member of the class of 3-phenyl hydantoin compounds described in U.S. Pat. No. 3,755,350 to Sauli. The effectiveness of iprodione to control the spread of snow mould in turfgrasses (especially the grey snow moulds *T. incarnate* and *T. ishikariensis*) is highly variable due to the varying amounts of fungus inoculums, the varying length of snow cover under which snow mould inoculums thrive and the varying winter temperatures that exist across the country from year to year. Thus, in order to effectively control against a spectrum of snow moulds a relatively high dose may be required as well as multiple applications.

Compass™ (trifloxystrobin; (αE)-α(methoxyimino)-2-[[[(E)-1-[3-(trifluoromethylphenyl)ethylidine]-amino]oxy] methyl]benzenacetic acid methyl ester) is an aromatic dioxime fungicide which has been approved for the control of leaf spot, *Fusarium* patch and brown patch diseases in turfgrass. Trifloxystrobin is a member of the class of aromatic dioxime fungicides described in U.S. Pat. No. 5,238,956 granted to Clough et al.

SUMMARY OF THE INVENTION

One aspect of the invention comprises a composition comprising a fungicidally effective amount of a compound have the general formula 1:

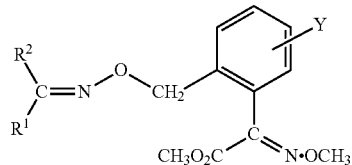

and stereoisomers thereof, wherein Y is hydrogen, halo, hydroxy, $C_{1-4}$ alkyl, $C_{1-4}$ alkoxy, $C_{1-4}$ haloalkyl, $C_{1-4}$ haloalkoxy, $C_{1-4}$ alkylcarbonyl, $C_{1-4}$ alkoxycarbonyl, phenoxy, nitro or cyano; $R_1$ and $R_2$, which may be the same or different, are hydrogen, optionally substituted alkyl, optionally substituted cycloalkyl, optionally substituted cycloalkylalkyl, optionally substituted aralkyl, optionally substituted aryloxyalkyl, optionally substituted arylthioalkyl, optionally substituted alkenyl, optionally substituted alkynyl, optionally substituted alkoxy, optionally substituted aryl, optionally substituted aryloxy, nitro, halo, cyano, —$NR_3R_4$, —$CO_2R_3$, —$CONR_3R_4$, —$COR_3$, —$S(O)_nR_3$ wherein n is 0, 1 or 2, $(CH_2)_mPO(OR^3)$ wherein m is 0 or l, or $R_1$ and $R_2$ join to form a carbocyclic ring system; and $R_3$ and $R_4$, which are the same or different, are hydrogen, optionally substituted alkyl, optionally substituted aralkyl, optionally substituted alkenyl, optionally substituted alkynyl or optionally substituted aryl, and a fungicidally effective amount of a compound having the general formula 2:

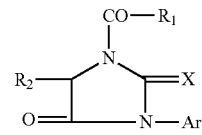

and stereoisomers thereof, wherein Ar represents phenyl or phenyl substituted with one to two substituents selected from the group consisting of chlorine, fluorine, alkyl of one to four carbon atoms and trifluoromethyl; $R_1$ represents alkoxy of one to four carbon atoms or —$NR_3R_4$. in which $R_3$ and $R_4$ represents hydrogen. alkyl of one to four carbon atoms or alkenyl of two to four carbon atoms; $R_2$ represents hydrogen or alkyl of one to four carbon atoms; and X represents oxygen or sulphur.

Preferably the composition comprises additional formulation constituents such as the commercial formulation constituents for Rovral Green GT™ and Compass™ as well as similar formulation constituents.

The composition may further comprise a carrier or diluent such as water. According to another aspect, the above compounds 1 and 2 are present in the composition in a molar ratio of between 9:1 and 30:1, and more preferably the molar ratio is between 14:1 and 25:1. The compositions according to the invention have useful fungicidal properties, including inhibiting the infection of turfgrass by a spectrum of snow moulds and in particular pink and gray snow moulds such as *M. nivale*, *T. incarnate*, and *T. ishikariensis*.

According to another aspect, the above compounds 1 and 2 are present in the composition in a molar ratio of between 1:1 and 6:1 and more preferably the molar ratio is between 2:1 and 5:1. The compositions according to the invention have useful fungicidal properties, including inhibiting the infection of turfgrass by dollar spot mould (*S. homeocarpa*).

According to another aspect of the invention, the compounds 1 and 2 comprise iprodione and trifloxystrobin for inhibiting the infection of turfgrass by a spectrum of snow moulds. According to another aspect, the composition is effective when applied such that less than 25% of a treated area of turfgrass is infected by snow mould, by applying the composition to turfgrass which is exposed to less than 120 days of snow cover annually.

According to another aspect of the invention, there is provided a method of using the composition on turfgrass to prevent the infection of snow moulds or dollar spot infections. In a further aspect the invention comprises the method of applying the composition according to the invention to turfgrass which is subsequently covered with a substantially impervious tarp. In this aspect, an equal or reduced amount of the active substances may be applied with generally equal effectiveness in comparison with untarped treatment.

In one aspect the invention comprises the application of formulae 1 and 2, preferably as a tank mixture but alternatively in succession, in an amount between $9.08 \times 10^{-2}$ and 0.273 moles, and $4.65 \times 10^{-3}$ and $1.40 \times 10^{-2}$ moles per 100 m$^2$. The said compounds are applied to turfgrass to combat one or more of *M. nivale*, *T. incarnata*, *T. ishikariensis* and *S. homeocarpa*. Preferably formulae 1 and 2 comprise iprodione and trifloxyxtrobin applied in an amount of between 30 and 90 g/100 m$^2$ and 1.9 and 5.7 g/100 m$^2$ respectively. Still more preferably formulae 1 and 2 comprise Rovral Green GT and Compass or similar commercial formulations.

In a further aspect the invention comprises application of compounds as described above followed by tarping of the field wherein the mould infection rate is reduced by at least 90 percent and preferably at least 95% in comparison with an untreated control. Preferably only a single application is applied for a given course of treatment.

In a still further aspect the invention comprises the compositions and methods as described above with a third active constituent comprising chlorothalonil (Daconil™).

While the invention will be described in conjunction with illustrated embodiments, it will be understood that it is not intended to limit the invention to such embodiments. On the contrary, it is intended to cover all alternatives, modifications and equivalents as may be included within the spirit and scope of the invention as defined by the present patent specification as a whole.

DETAILED DESCRIPTION OF THE PREFERRED EMBODIMENTS

Figure 1:
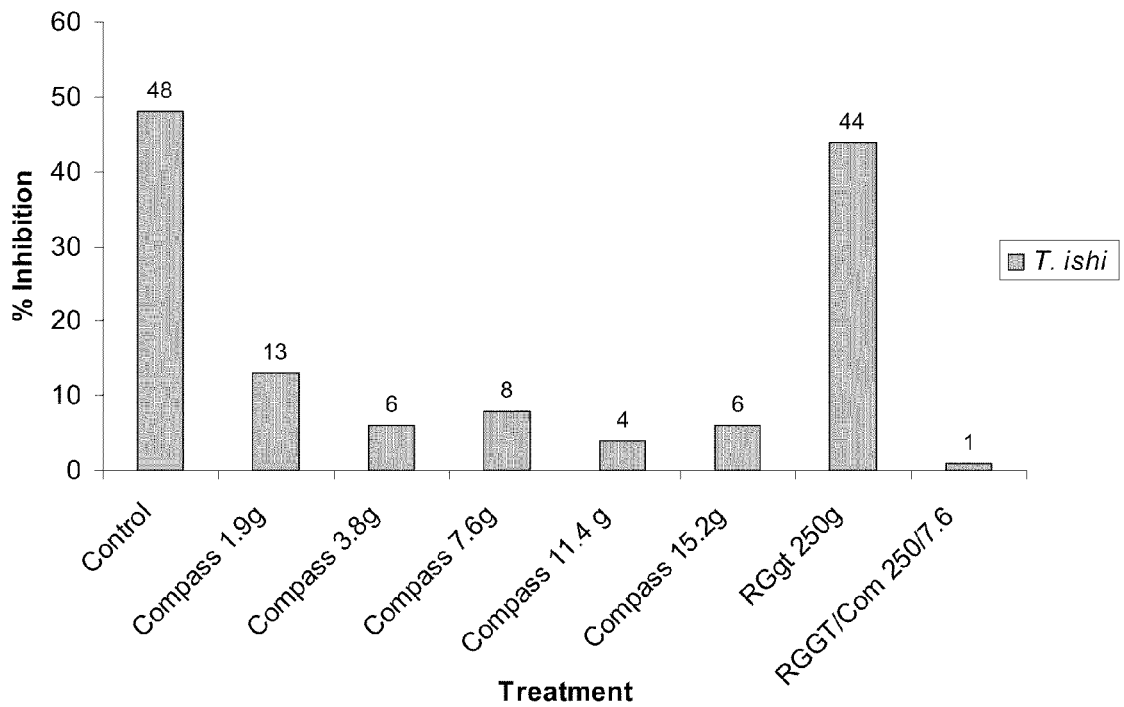
FIGS. 1 through 6 illustrate test results for three snow mould funguses, *T. ishikariensis*, *M. nivale*, and *T. incarnate*, on plots covered with snow for approximately 100 days (FIGS. 1 & 2), approximately 120 days (FIGS. 5 & 6), or trial tarped for 4 months to simulate snow cover. Plots covered with snow had natural snow mould infection, while tarped plots were inoculated with the fungus indicated. The graphs illustrate the percentage of snow mould infection on the tested plot, for different application strengths (in g per 100 m$^2$) of Compass™, Rovral Green GT™ ("RG GT"), alone and in combination.
Figure 2:
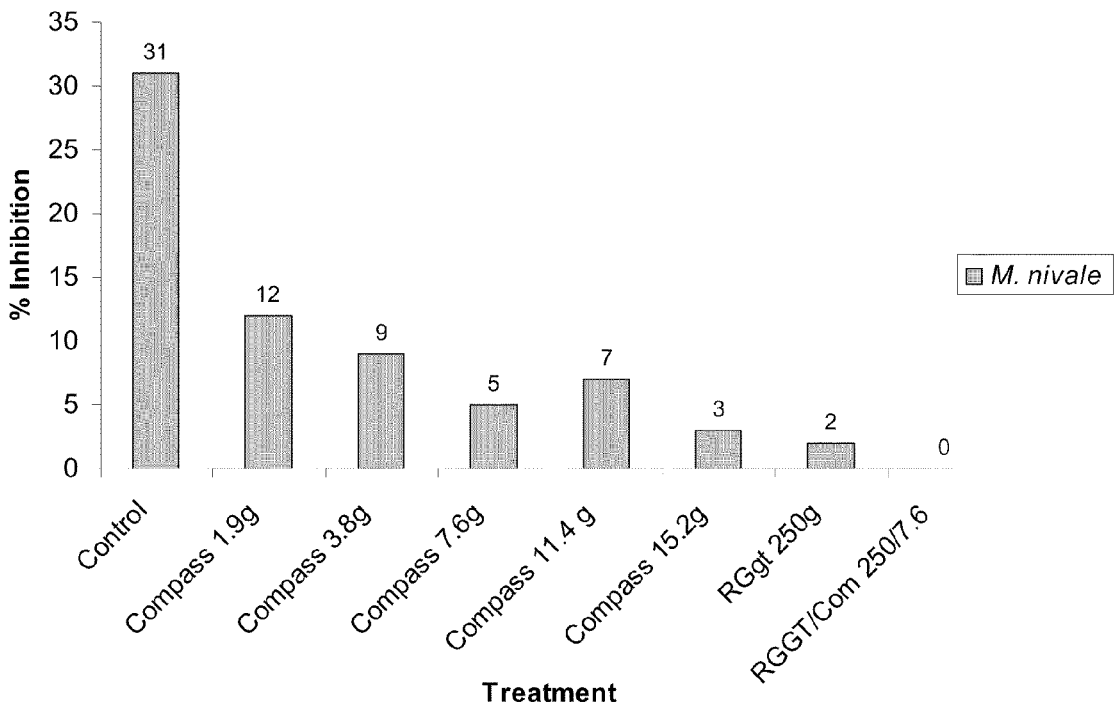
Figure 3:
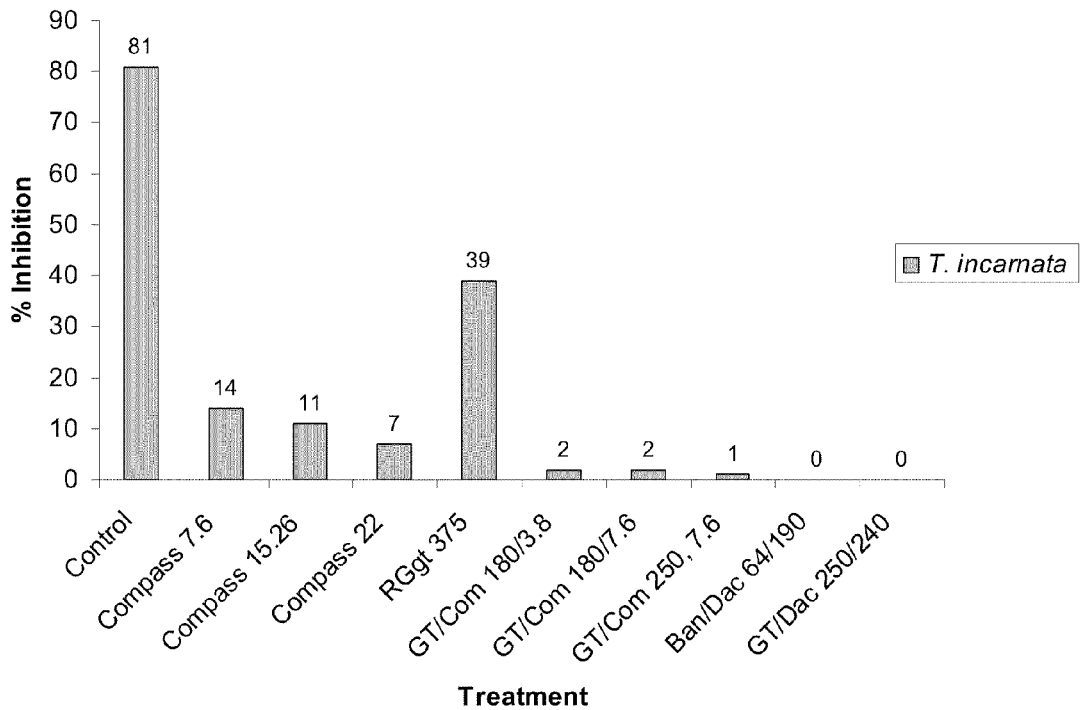
Figure 4:
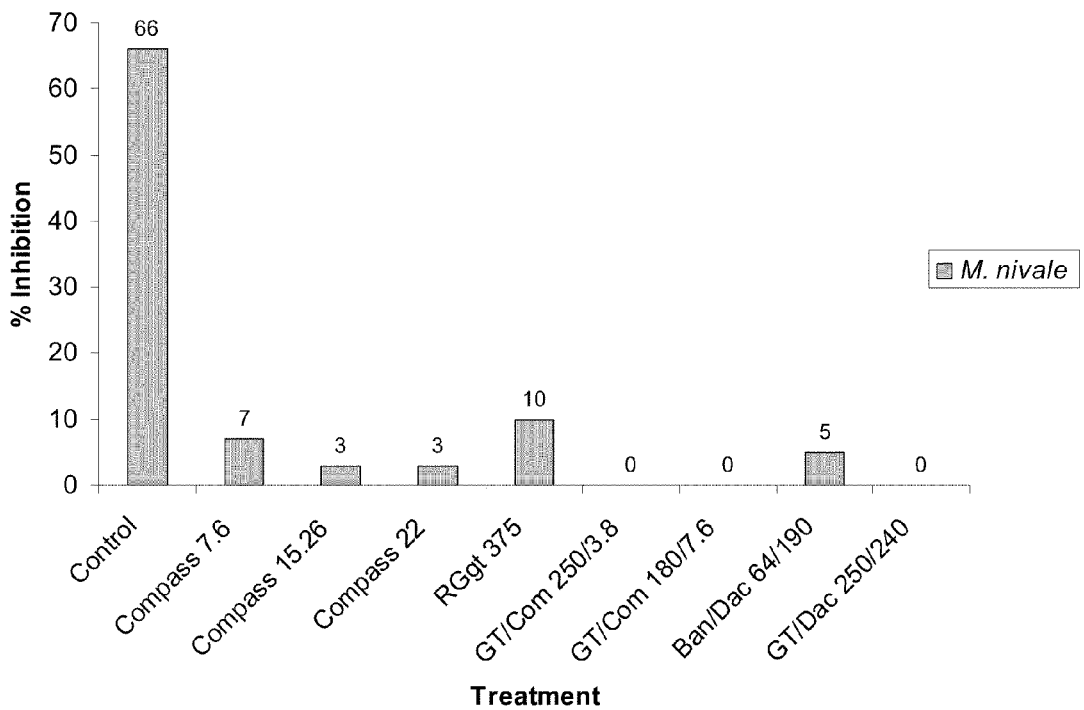
Figure 5:
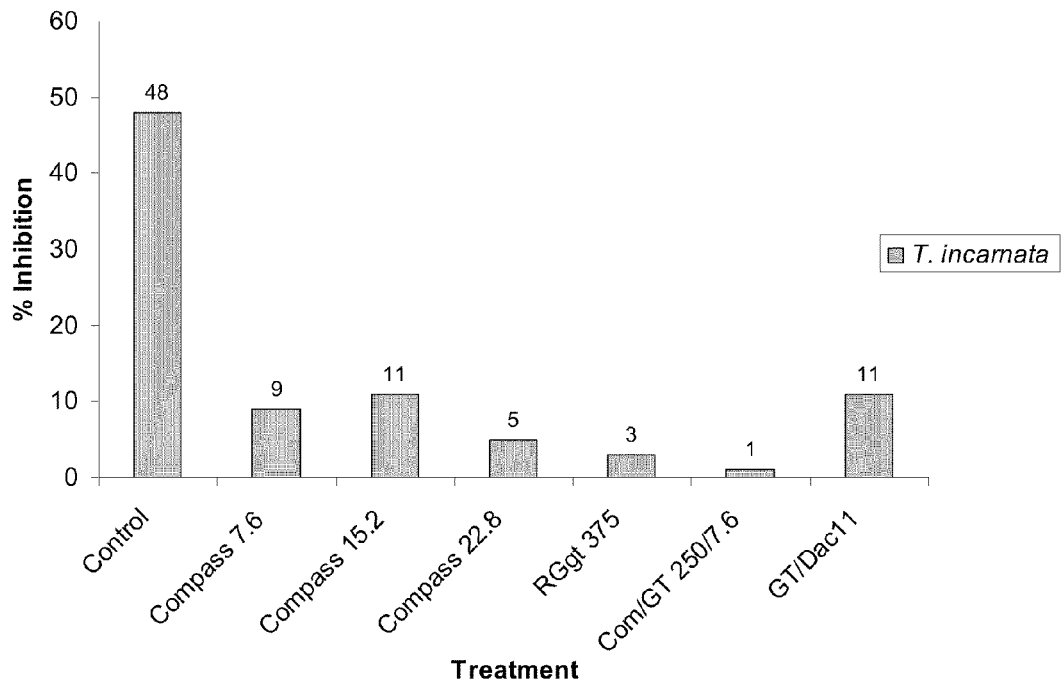
Figure 6:
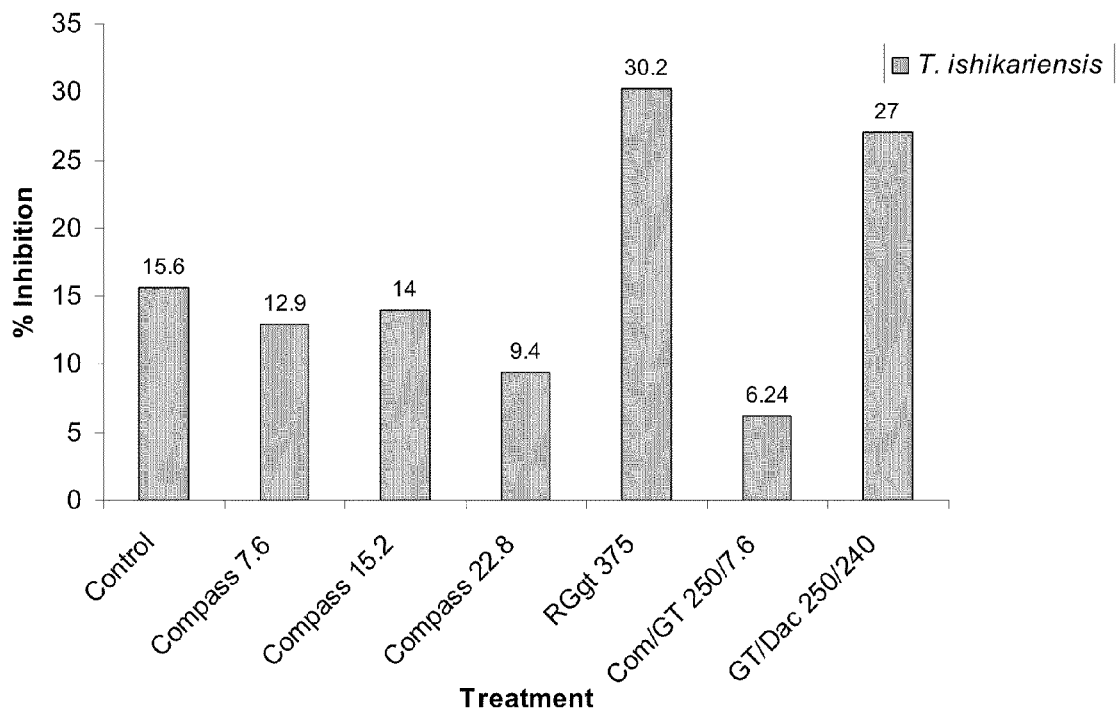

A composition may be prepared comprising a mixture of iprodione and trifloxystrobin in the ratio of about 16:1 (w:w) in an aqueous solution, by combining suitable amounts of commercial formulations of Rovral Green GT™ and Compass™. The said ratio comprises a calculated molar ratio of about 19.53:1. The composition may be diluted sufficiently for application on turfgrass at a rate of between 30 and 90 g per 100 m$^2$ iprodione and between 1.9 g and 5.7 g per 100 m$^2$ trifloxystrobin.

A composition may be prepared comprising a mixture of iprodione and trifloxystrobin in the ratio of about 3:1 (w:w) in an aqueous solution, by combining suitable amounts of commercial formulations of Rovral Green GT™ and Compass™. The said ratio comprises a calculated molar ratio of about 3.93:1. The composition may be diluted sufficiently for application on turfgrass at a rate of between 4.92 and 14.76 g per 100 m$^2$ iprodione and between 1.55 g and 4.65 g per 100 m$^2$ trifloxystrobin.

The composition may be applied to turfgrass plots in different geographic zones in Canada, including the region subject to more than 150 days of substantially continuous snow cover, and regions subject to between 90 and 120 days of substantially continuous snow cover. Chemical treatments were applied in the late fall at the rate described above, and assessments of snow plots were taken in the spring, after snow cover had melted off of the trial plots.

FIGS. 1 through 6 illustrate test results for three snow mould funguses, *T. ishikariensis*, *M. nivale*, and *T. incarnate*, on plots covered with snow for approximately 100 days (FIGS. 1 & 2), approximately 120 days (FIGS. 5 & 6), or trial tarped for 4 months to simulate snow cover. Plots covered with snow had natural snow mould infection, while tarped plots were inoculated with the fungus indicated. The graphs illustrate the percentage of snow mould infection on the tested plot, for different application strengths (in g per 100 m$^2$) of Compass™, Rovral Green GT™ ("RG GT"), alone and in combination.

It was found that a tank mix for application of 250 ml Rovral Green GT™ (per 100 m$^2$) and 7.6 g of Compass™ (per 100 m$^2$) provided approximately 99% control of *T. incarnate*, and about 92% control of *T. ishikariensis*, and 97% control of *M. nivale*. The tank mixtures described herein thus lead to more inhibition than similar amounts applied separately of the above components to different plots. Thus, there exists synergy in the mixture described above, thereby permitting greater inhibition with a lower dosage rate. In the examples herein, the Compass formulation comprises 50% active substance. Further, in several of the above examples tarped and untarped fields were tested with the tarped fields requiring no greater amount of the composition to achieve effective inhibition.

Example 2

A trial was conducted in a region in Canada having a substantially continuous snow cover duration of more than 150 days, with relatively high disease pressure. The mixture of Rovral Green GT™ at 250 ml and Compass™ at 7.6 g (per 100 m²) was applied prior to snow cover, and an assessment conducted after snow melt. Two applications of the mixture and controls were applied about 10 days apart. After snow melt, the percentage disease spread of T. ishikariensis and M. nivale were detected. The Rovral Green GT™ and Compass™ mixture resulted in about 25% disease cover, while Rovral Green GT™ at the higher dose rate of 360 ml per 100 m² (recommended treatment level) resulted in 71.25% disease cover, while Compass™ at 7.6 g per 100 m² resulted in 78.75% disease cover.

Example 3

Three different turfgrass plots infected with dollar spot mould (S. homeocarpa) in three different locations was treated with one of 3.1 g of Compass™ ("Comp")/100 m², 4.6 g of Compass™/100 m², 62 ml of Rovral Green GT™ ("GT") or a combination of 3.1 g/41 ml Compass™/Rovral Green GT™/100 m² on either 14, 21 or 20-21 day intervals.

Figure 7:
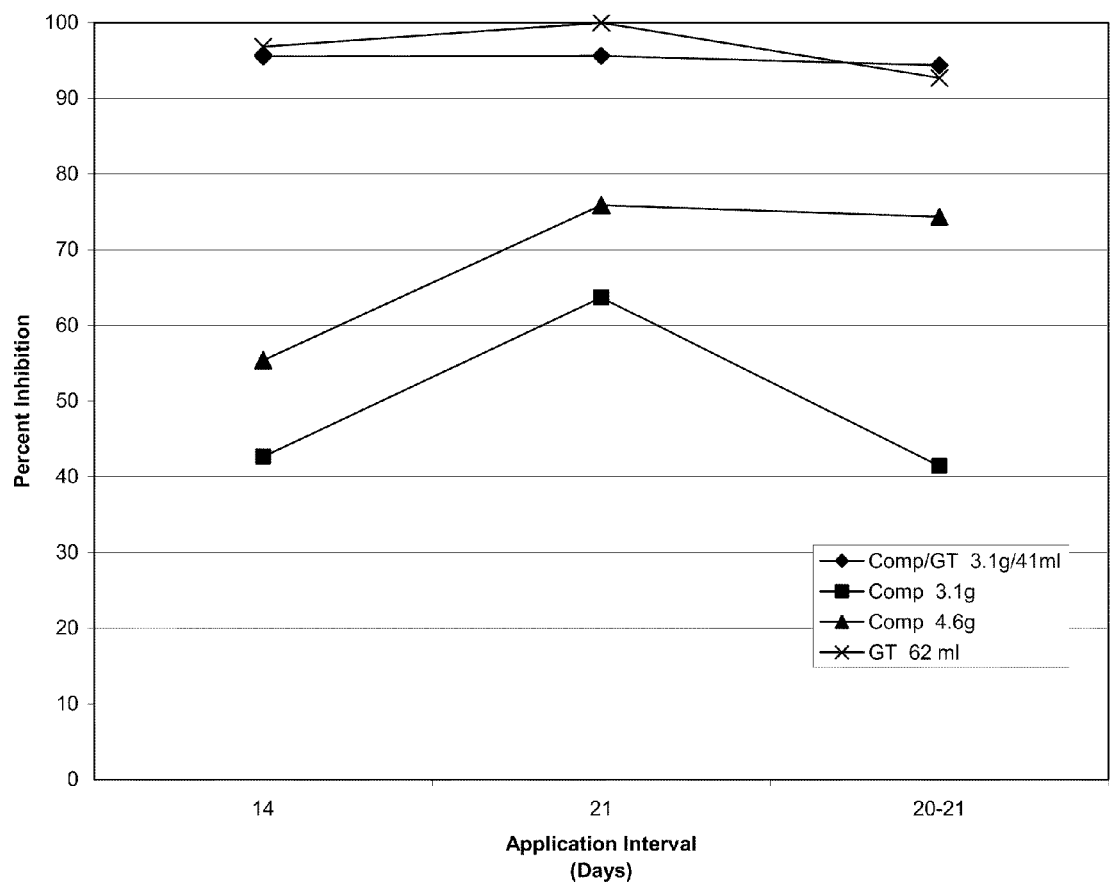
FIG. 7 illustrates the percentage of *S. homeocarpa* inhibition as compared to an untreated test plot, for each of the different application strengths (in g per 100 m$^2$) of Compass™, Rovral Green GT™, alone and in combination.

FIG. 7 illustrates the percentage of S. homeocarpa inhibition as compared to an untreated test plot, for each of the different application strengths (in g per 100 m²) of Compass™, Rovral Green GT™, alone and in combination.

Fungicidal compositions according to the invention may be supplied in a concentrated liquid, powder or granular form or any other form commonly used in the agricultural industry. The fungicidal composition may also be supplied in combination as a pre-mix to be diluted to the correct concentration or supplied as individual components to be combined in a tank mixture. Preferably the compositions are diluted with water but other suitable diluents are possible. Other active or inactive constituents may also be added.

Although the tested embodiments relate to tank mixtures, improved results may also be obtained by separately applying the two active components in close time proximity.

Although this invention has been described in terms of a preferred embodiment, other embodiments that are apparent to those of ordinary skill in the art are also within the scope of this invention. Accordingly, the scope of the invention is limited only in scope by the following claims and functional equivalents thereof.

The invention claimed is:

1. A method of treating turfgrass to reduce the growth of fungus on the turfgrass, comprising the steps of:
   (a) providing a composition comprising a fungicidally effective amount of a compound of formula 1:

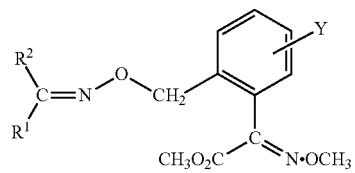

and stereoisomers thereof, wherein

Y is hydrogen, halo, hydroxy, $C_{1-4}$ alkyl, $C_{1-4}$ alkoxy, $C_{1-4}$ haloalkyl, $C_{1-4}$ haloalkoxy, $C_{1-4}$ alkylcarbonyl, $C_{1-4}$ alkoxycarbonyl, phenoxy, nitro or cyano;

$R^1$ and $R^2$, which may be the same or different, are hydrogen, optionally substituted alkyl, optionally substituted cycloalkyl, optionally substituted cycloalkylalkyl, optionally substituted aralkyl, optionally substituted aryloxyalkyl, optionally substituted arylthioalkyl, optionally substituted alkenyl, optionally substituted alkynyl, optionally substituted alkoxy, optionally substituted aryl, optionally substituted aryloxy, nitro, halo, cyano, —$NR^3R^4$, —$CO_2R^3$, —$CONR^3R^4$, —$COR^3$, —$S(O)_nR^3$ wherein n is 0, 1 or 2, $(CH_2)_mPO(OR^3)$ wherein m is 0 or I, or $R^1$ and $R^2$ join to form a carbocyclic ring system; and $R^3$ and $R^4$, which are the same or different, are hydrogen, optionally substituted alkyl, optionally substituted aralkyl, optionally substituted alkenyl, optionally substituted alkynyl or optionally substituted aryl, and, a fungicidally effective amount of a compound of formula 2:

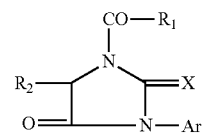

and stereoisomers thereof, wherein

Ar represents phenyl or phenyl substituted with one to two substituents selected from the group consisting of chlorine, fluorine, alkyl of one to four carbon atoms and trifluoromethyl;

$R_1$ represents alkoxy of one to four carbon atoms or —$NR^3R^4$, in which $R^3$ and $R^4$ represents hydrogen alkyl of one to four carbon atoms or alkenyl of two to four carbon atoms;

$R_2$ represents hydrogen or alkyl of one to four carbon atoms; and

X represents oxygen or sulphur;

(b) diluting said composition within a diluent; and
(c) applying said diluted composition at least once to said turfgrass.

2. A method as defined in claim 1, wherein said fungus comprises snow mould and wherein said composition is applied prior to the onset of snow cover on said turfgrass.

3. A method as defined in claim 2, wherein said snow mould is selected from one or more of M. nivale, T. incarnata, and T. ishikariensis.

4. A method as defined in claim 1, wherein said fungus is S. homeocarpa.

5. A method as defined in claim 1, wherein said formula 1 comprises trifloxystrobin.

6. A method as defined in claim 1, wherein said formula 2 comprises iprodione.

7. A method as defined in claim 1, wherein said formulae 1 comprises trifloxystrobin and said formulae 2 comprises iprodione.

8. A method as defined claim 7, wherein said trifloxystrobin and iprodione are present in a molar ratio of between 1:1 and 1:30 of trifloxystrobin: iprodione.

9. A method as defined in claim 8, wherein said trifloxystrobin and iprodione are present in a molar ratio of between 1:1 and 1:6 of trifloxystrobin: iprodione.

10. A method as defined in claim 8, wherein said trifloxystrobin and iprodione are present in a molar ratio of between 1:2 and 1:5 of trifloxystrobin: iprodione.

11. A method as defined in claim 1, further comprising the step of covering the treated turfgrass with a substantially impervious tarp.

12. A method as defined in claim 1, wherein the diluted composition is applied only a single time to the turfgrass prior to snow cover.

13. A method as defined in claim 1, wherein the diluted composition is applied at least once after the snow cover has gone.

14. A method as defined in claim 1, wherein the diluted composition is applied more than once prior to snow fall to the turfgrass in areas receiving greater than 120 days of snow cover.

15. A method as defined in claim 1, wherein the composition further comprises a fungicidally effective amount of chlorothalonil.

16. A method of treating turfgrass to reduce the growth of fungus on the turfgrass, comprising the steps of:
(a) providing a composition consisting essentially of a fungicidally effective amount of a compound of formula 1:

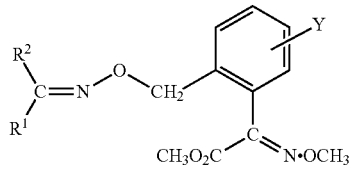

and stereoisomers thereof, wherein
Y is hydrogen, halo, hydroxy, $C_{1-4}$ alkyl, $C_{1-4}$ alkoxy, $C_{1-4}$ haloalkyl, $C_1$haloalkoxy, $C_{1-4}$ alkylcarbonyl, $C_{1-4}$ alkoxycarbonyl, phenoxy, nitro or cyano;
$R^1$ and $R^2$, which may be the same or different, are hydrogen, optionally substituted alkyl, optionally substituted cycloalkyl, optionally substituted cycloalkylalkyl, optionally substituted aralkyl, optionally substituted aryloxyalkyl, optionally substituted arylthioalkyl, optionally substituted alkenyl, optionally substituted alkynyl, optionally substituted alkoxy, optionally substituted aryl, optionally substituted aryloxy, nitro, halo, cyano, $-NR^3R^4$, $-O_2R^3$, $-CONR^3R^4$, $-COR^S$, $-S(O)_nR^3$ wherein n is 0, 1 or 2, $(CH_2)_mPO(OR^3)$ wherein m is 0 or 1, or $R^1$ and $R^2$ join to form a carbocyclic ring system; and
$R^3$ and $R^4$, which are the same or different, are hydrogen, optionally substituted alkyl, optionally substituted aralkyl, optionally substituted alkenyl, optionally substituted alkynyl or optionally substituted aryl, and,
a fungicidally effective amount of a compound of formula 2:

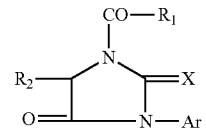

and stereoisomers thereof, wherein
Ar represents phenyl or phenyl substituted with one to two substituents selected from the group consisting of chlorine, fluorine, alkyl of one to four carbon atoms and trifluoromethyl;
$R_1$ represents alkoxy of one to four carbon atoms or $-NR^3R^4$, in which $R^3$ and $R^4$ represents hydrogen. alkyl of one to four carbon atoms or alkenyl of two to four carbon atoms;
$R_2$ represents hydrogen or alkyl of one to four carbon atoms; and
X represents oxygen or sulphur;
(b) diluting said composition within a diluent; and
(c) applying said diluted composition at least once to said turfgrass.

17. A method according to claim 16, wherein said compound of formula 1 comprises trifloxystrobin and said compound of formula 2 comprises iprodione.

18. A method according to claim 17, wherein said trifloxystrobin and iprodione are present in a molar ratio of between 1:1 and 1:30 of trifloxystrobin: iprodione.

19. A method according to claim 17, wherein said trifloxystrobin and iprodione are present in a molar ratio of between 1:2 and 1:5 of trifloxystrobin: iprodione.

20. A method according to claim 1, wherein the composition is present as a suspension concentrate.

* * * * *